US007383164B2

(12) United States Patent
Aram et al.

(10) Patent No.: US 7,383,164 B2
(45) Date of Patent: Jun. 3, 2008

(54) SYSTEM AND METHOD FOR DESIGNING A PHYSIOMETRIC IMPLANT SYSTEM

(75) Inventors: Luke Aram, Warsaw, IN (US); Daniel Auger, Fort Wayne, IN (US); Jordan Lee, Warsaw, IN (US); Adam Hayden, Fort Wayne, IN (US)

(73) Assignee: DePuy Products, Inc., Warsaw, IN (US)

( * ) Notice: Subject to any disclaimer, the term of this patent is extended or adjusted under 35 U.S.C. 154(b) by 587 days.

(21) Appl. No.: 10/806,637

(22) Filed: Mar. 23, 2004

(65) Prior Publication Data

US 2005/0197814 A1 Sep. 8, 2005

Related U.S. Application Data

(60) Provisional application No. 60/550,713, filed on Mar. 5, 2004.

(51) Int. Cl.
*G06F 9/455* (2006.01)

(52) U.S. Cl. ........................... 703/7; 703/11; 600/594; 600/300; 600/587; 606/1; 606/102; 606/53; 606/71; 623/18.11; 623/17.16

(58) Field of Classification Search .................... 703/7, 703/11; 424/50; 606/53, 71; 623/16.11, 623/20.14, 17.14, 17.12, 18.11; 600/587, 600/300, 594, 1; 607/116
See application file for complete search history.

(56) References Cited

U.S. PATENT DOCUMENTS

| | | | | |
|---|---|---|---|---|
| 4,436,684 | A | 3/1984 | White | 264/138 |
| 4,936,862 | A | 6/1990 | Walker et al. | 128/898 |
| 5,362,996 | A | 11/1994 | Yizraeli | 326/27 |
| 5,448,489 | A | 9/1995 | Reuben | 700/163 |
| 5,488,952 | A | 2/1996 | Schoolman | 104/251 |
| 5,522,402 | A | 6/1996 | Cooley | 600/595 |
| 5,610,966 | A | 3/1997 | Martell et al. | 382/187 |
| 5,741,215 | A | 4/1998 | D'Urso | 600/407 |
| 5,798,924 | A | 8/1998 | Eufinger et al. | 700/117 |
| 6,002,859 | A | 12/1999 | DiGioia, III et al. | 514/14 |
| 6,126,690 | A | 10/2000 | Ateshian et al. | 623/224 |
| 6,144,385 | A | 11/2000 | Girard | 345/424 |
| 6,161,080 | A | 12/2000 | Aouni-Ateshian et al. | 703/11 |
| 6,177,034 | B1 | 1/2001 | Ferrone | 264/40.1 |
| 6,205,411 | B1 * | 3/2001 | DiGioia et al. | 703/11 |
| 6,254,639 | B1 | 7/2001 | Peckitt | 623/11.11 |
| 6,280,474 | B1 * | 8/2001 | Cassidy et al. | 623/16.11 |

(Continued)

FOREIGN PATENT DOCUMENTS

| | | |
|---|---|---|
| GB | 2 382 777 | 6/2003 |

*Primary Examiner*—Paul Rodriguez
*Assistant Examiner*—Kandasamy Thangavelu
(74) *Attorney, Agent, or Firm*—Maginot, Moore & Beck

(57) ABSTRACT

A system improves the design of artificial implant components for use in joint replacement surgeries. The system includes an anthropometric static image data analyzer, an implant model data generator, a kinematic model simulator, and a dynamic response data analyzer. The implant model data generator may also use image data of a joint in motion for modification of the implant model data used in the kinematic simulation. Dynamic response data generated by the kinematic model simulation is analyzed by the dynamic response data analyzer to generate differential data that may be used to further refine the implant model data.

29 Claims, 10 Drawing Sheets

U.S. PATENT DOCUMENTS

| | | | | |
|---|---|---|---|---|
| 6,458,161 | B1 | 10/2002 | Gibbs et al. | 623/22.32 |
| 6,459,943 | B1 | 10/2002 | Suetani et al. | 700/96 |
| 6,530,956 | B1 * | 3/2003 | Mansmann | 623/18.11 |
| 6,674,883 | B1 | 1/2004 | Wei et al. | 382/132 |
| 6,750,866 | B1 | 6/2004 | Anderson, III | 345/474 |
| 6,793,496 | B2 | 9/2004 | Edic et al. | 434/262 |
| 6,799,066 | B2 | 9/2004 | Steines et al. | 600/407 |
| 7,027,874 | B1 * | 4/2006 | Sawan et al. | 607/116 |
| 7,029,479 | B2 * | 4/2006 | Tallarida et al. | 606/102 |
| 2002/0035400 | A1 * | 3/2002 | Bryan et al. | 623/17.15 |
| 2002/0115944 | A1 * | 8/2002 | Mendes et al. | 600/594 |
| 2002/0128715 | A1 * | 9/2002 | Bryan et al. | 623/17.15 |
| 2003/0097182 | A1 * | 5/2003 | Buchman et al. | 623/18.11 |
| 2003/0135277 | A1 * | 7/2003 | Bryan et al. | 623/17.12 |
| 2003/0157187 | A1 * | 8/2003 | Hunter | 424/600 |
| 2004/0015170 | A1 * | 1/2004 | Tallarida et al. | 606/71 |
| 2004/0071637 | A1 * | 4/2004 | Elia | 424/50 |
| 2004/0092928 | A1 * | 5/2004 | Sasso | 606/53 |
| 2004/0093084 | A1 * | 5/2004 | Michelson | 623/17.11 |
| 2004/0138591 | A1 * | 7/2004 | Iseki et al. | 600/587 |
| 2004/0143332 | A1 * | 7/2004 | Krueger et al. | 623/17.14 |
| 2004/0148030 | A1 * | 7/2004 | Ek | 623/20.14 |
| 2004/0152955 | A1 * | 8/2004 | McGinley et al. | 600/300 |
| 2004/0176851 | A1 * | 9/2004 | Zubok et al. | 623/17.15 |
| 2004/0267242 | A1 * | 12/2004 | Grimm et al. | 606/1 |
| 2005/0033439 | A1 * | 2/2005 | Gordon et al. | 623/17.16 |
| 2006/0167550 | A1 * | 7/2006 | Snell et al. | 623/17.13 |
| 2006/0167559 | A1 * | 7/2006 | Johnstone et al. | 623/23.41 |

* cited by examiner

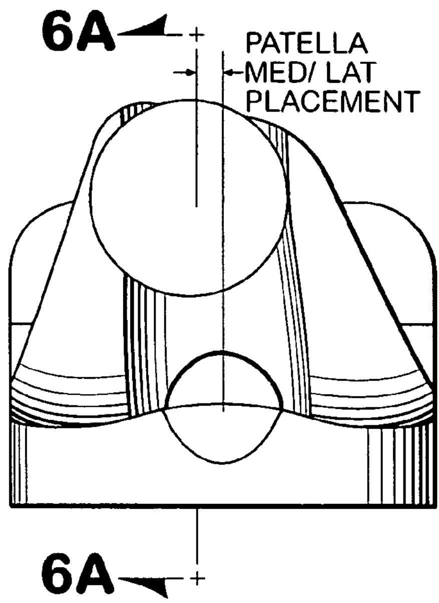
FIG 6
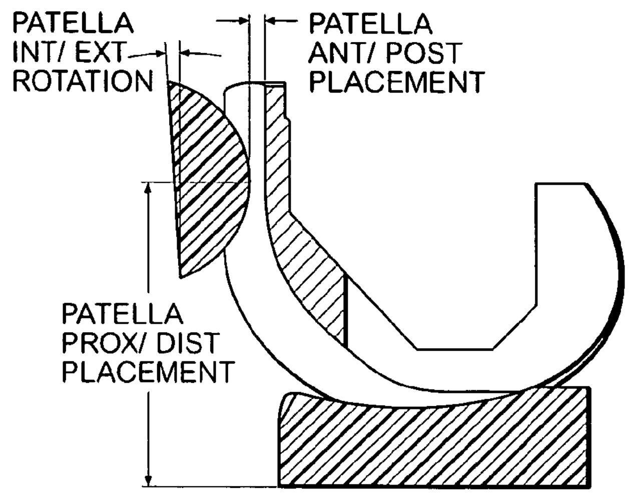
FIG 6A
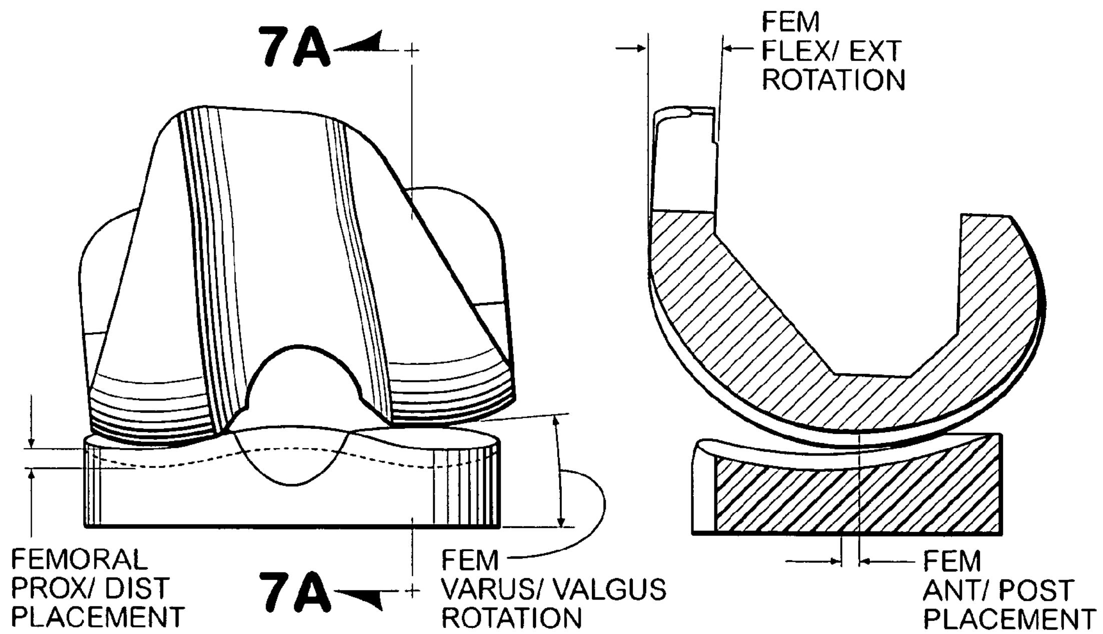
FIG 7
FIG 7A

| | LOW | MEDIUM | HIGH | UNIT |
|---|---|---|---|---|
| Sagital Conformity | 1/1.41 | 1.27/8.41 | 1.54/15.4 | R(Femur) / R(Tibia) |
| S3 | 17.4 | 21.35 | 25.3 | mm |
| S2 | 31.6 | 39.1 | 46.6 | mm |
| ACL Retention | N | N | Y | |
| Patella Track Radii | 23.5 | 29.7 | 35.9 | mm |
| PCL Retention | N | Y | Y | |
| AP Placement of Patella Track | -2 | 0 | 2 | mm |
| Femoral Flex/Ext Rotation | -3 | 0 | 3 | degrees |
| Femoral Ant/Post Placement | -3 | 0 | 3 | mm |
| Fem Prox/Dist Placement | -3 | 0 | 3 | mm |
| Tib Ant/Post Rotation | 0 | 3 | 6 | degrees |
| Tib Prox/Dist Placement | -3 | 0 | 3 | mm |
| Patella Flex/Ext Rotation | -3 | 0 | 3 | degrees |
| Patella Ant /Post Placement | -3 | 0 | 3 | mm |
| Patella Prox/Dist Placement | -3 | 0 | 3 | mm |
| Fixed or Mobile | F | F | M | |
| Coronal Conformity | 3 | 2 | 1 | R(Femur) / R(Tibia) |
| Sulcus Angle | 0 | 3.5 | 7 | degrees |
| Coronal Radii | 14.6 | 26.65 | 38.7 | mm |
| Divergence of Condyles | 0 | 0 | 6 | degrees |
| Condyle Asymmetry | N | N | Y | |
| Patella Design (Anatomic RP or Dome FP) | Dome | Dome | Anatomic | |
| Ant/Post Placement of the Dwell Point on the Tibia | 0.989 | 1.2145 | 1.44 | mm |
| Femoral Varus/Valgus Rotation | -3 | 0 | 3 | degrees |
| Femoral Int/Ext Rotation | 0 | 3 | 6 | degrees |
| Tibial Varus/Valgus Rotation | -3 | 0 | 3 | degrees |
| Tibial Int/Ext Rotation | -3 | 0 | 3 | degrees |
| Tibial Med/Lat Placement | -3 | 0 | 3 | mm |
| Patella Int/Ext Rotation | -3 | 0 | 3 | degrees |
| Patella Med/Lat Placement | -3 | 0 | 3 | mm |

FIG 10

SYSTEM AND METHOD FOR DESIGNING A PHYSIOMETRIC IMPLANT SYSTEM

CLAIM OF BENEFIT OF PRIORITY

This application claims the benefit of priority under 35 U.S.C. 119(e) from Provisional Patent Application entitled System and Method for Designing a Physiometric Implant System, filed on Mar. 5, 2004, and assigned Ser. No. 60/550,713.

FIELD OF THE INVENTION

This invention relates to implant design systems and, more particularly, to systems for designing implants for joint replacement surgeries.

BACKGROUND OF THE INVENTION

Joints in the body have compartments with articulating surfaces that move against or in close proximity with other components in the joint. For example, the knee joint includes the distal femur that cooperates with both the patella and proximal tibia and, if present, a fabella. The distal femur has a lateral and medial condyle that rotates in moving relationship to the lateral and medial meniscus of the tibia. Bone disease, such as arthritis, may deteriorate one or more joint compartments so that movement in the joint produces pain. One remedy for joints deteriorated by disease or injury is replacement of one or more compartments of the joint with artificial implants. For example, a total knee replacement (TKR) may be performed by surgically opening the knee, removing the diseased portions of the distal femur, proximal tibia, and/or pattelar surface, and implanting an artificial prosthesis. The bio-compatible materials used to make the bone prosthesis reduce the risk of infection and wear well.

One important aspect of using artificial implants to repair a diseased joint is the fit of the artificial implants with one another and the patient's joint physiology. That is, implant size, shape, and location are important parameters for enabling patient movement that complies with the ligaments and muscles of the patient. Producing implants with the appropriate parameter values may determine whether a patient regains full function and mobility in the joint following the replacement surgery. Ideally, the components for a joint replacement would be customized for a patient's particular joint physiology. However, customizing every artificial implant component for a replacement surgery would significantly increase the cost of fabrication and coordination of component production with surgical resources would be difficult.

One way of addressing the need to provide artificial implants that can be accommodated by a patient's physiology is to provide a finite number of artificial implants that accommodate a range of characteristics for the bones of commonly replaced joints. To design these artificial implant models, statistical data regarding the measurements of bone dimensions are collected for a sample population to determine the range and variability of bone dimensions that need to be accommodated in the general population. A hospital or surgery center may then keep an inventory of the various joint implant models to be ready to meet the needs of the patients undergoing joint replacement surgery.

One problem with this approach is the fit required for a complete range of motion for the joint. The natural variations in joints among people and the abundance of soft tissue structures for an indeterminate multiplicity of load sharing possibilities result in measurably different movements. An artificial implant must work together with a patient's soft tissues so a joint may achieve its proper motion. Thus, the artificial implant should closely represent a patient's articular geometry.

What is needed is a way of designing artificial implant components so that physiological movement is incorporated in the design and dimensions of the artificial implants.

What is needed is a way of designing artificial implants so that dynamic movement of a joint does not interfere with the smooth operation of articulating surfaces of artificial implants.

SUMMARY OF THE INVENTION

The above limitations of previously known systems and methods for designing artificial implants used in joint replacement surgeries have been overcome by a system and method operating in accordance with the principles of the present invention. The inventive system includes an anthropometric image data analyzer for identifying a plurality of geometric dimensions and a range of values for the identified dimensions, an implant model generator for generating at least one set of model data representative of the identified geometric dimensions and a group of values with the range of values for the identified dimensions, and a kinematic model simulator for incorporating a set of model data in a kinematic model of a joint so that the kinematic model simulator generates dynamic response data corresponding to the set of model data whereby the dynamic response of an artificial implant corresponding to the set of model data may be evaluated.

The dynamic response data may be evaluated by a dynamic response data analyzer to generate differential dimensional data for modifying the set of model data in response to the dynamic response data indicating that the artificial implant corresponding to that set of model data produces a conditional parameter in the kinematic model of the kinematic model simulator. The implant model generator incorporates the differential dimensional data to generate a second set of model data that is provided to the kinematic model simulator. The kinematic model simulator incorporates the second set of model data within the kinematic model to generate dynamic response data that corresponds to the second set of model data and the dynamic response data analyzer determines whether additional differential dimensional data are generated for modification of the second set of model data. This process may continue until the dynamic response data analyzer determines that a set of model data has been generated that is within acceptance parameters. The set of model data produced by this process may be used to manufacture an artificial implant component that has an improved prognosis for good fit and motion within a reconstructed joint.

The conditional parameter may be motion interference, economy of motion, reduction of jerk, normality of ligament tension, evenness of load sharing, minimization of energy consumption, path matching of motion, limited motion envelope, dynamic stability, reduced sensitivity to a change such as soft tissue injury or degradation, avoidance of stress peaks, controlled stress pattern, improved bone growth response, and optimal fitting. A conditional parameter for a kinematic simulation may incorporate one or more of these parameters.

The anthropometric data analyzer receives image data representing a plurality of joints. These image data may be computed tomography (CT) image data, magnetic resonance image (MRI) data, or other similar data. The anthropometric data analyzer may perform a frequency distribution analysis on the anthropometric data to generate groupings of joint compartment dimensions. The groupings may be provided to the implant model generator for development of one or more implant model data sets. In one embodiment of the present invention, the anthropometric data analyzer may include a static image data analyzer, which may be a known computer aided design (CAD) program. The CAD program enables an operator to select features in a static image for defining a geometric dimension and then measuring the selected geometric dimension. By defining multiple geometric dimensions and measuring the dimensions, the program generates a plurality of anthropometric dimensional data sets on which a frequency distribution may be performed. In another embodiment of the present invention, the anthropometric data analyzer includes a computer program that uses curve and surface fitting models. These curve and surface fitting models compensate for the more irregular geometries that occur in three dimensional representations. Static image data are image data of a joint held in a particular position and may be two dimensional static image data or three dimensional static image data or both. For example, two dimensional CT scan data may be compiled by a three dimensional static image data analyzer into voxel data to form a three dimensional image of a joint. Also, standard X-ray data for a joint image may be analyzed by the anthropometric data analyzer of the present invention to generate data sets for the implant model generator. The three dimensional static image data analyzer may include an adaptation of a computer program that measures terrain topographic features from satellite or laser survey imaging data.

The implant model generator may be the known CAD program discussed above that uses the frequency distribution groupings of the geometric dimensions and dimensional measurement data to generate at least one set of model data for a solid model of an artificial implant component. The implant model generator may generate at least one set of model data for each of the data groupings received from the anthropometric data analyzer. In this manner, implant models are generated that more closely correspond to a spectrum of possible patients than those models that are generated from a statistical average over the entire set of anthropometric data generated by the anthropometric data analyzer.

To further adapt an implant model to particular patient geometries, the implant model generator may use fluoroscopic or other dynamic image data for a plurality of patient joints in dynamic motion. These data may be used to verify that a set of model data generated by the implant model generator enables the components of the joint to move without causing a conditional parameter. If an undesired conditional parameter occurs, dimensional adjustments may be made to the implant model to reduce the likelihood that the conditional parameter occurs. For example, fluoroscopic data may be compiled by taking fluoroscopic X-ray images of one or more patient joints in motion. These images are two dimensional images of the relationship between joint components as the joint is moved. The implant model generator maps that dynamic response data into a set of positions for the components corresponding to the set of model data. This enables the implant model generator to determine whether the dimensions represented by the set of model data need modification to attenuate a conditional parameter that appears likely when the model components are in one of the relationships depicted in the dynamic response data. The set of model data generated by the model generator may be used to fabricate a solid model of an artificial implant component that corresponds to the geometric dimensions and measurements of the model data set. However, the system of the present invention also includes the kinematic model simulator for generating a more robust set of dynamic response data so that the dynamic response of the model data may be better evaluated. Furthermore, as explained in more detail below, the fluoroscopic data may be used to generate a patient model simulator for generating emulation force parameters for the kinematic model simulation.

The kinematic model simulator is a computer program that simulates a joint in motion. Preferably, the kinematic model simulator is based upon accurate computer modeling of at least one person's joint motion during various movements of the joint. The kinematic model simulator provides force vectors that operate at known positions on the simulated joint geometry. These force vectors represent the force applied at different times during a particular motion to a joint compartment component. For example, a set of force vectors may be used to represent the force applied at a particular ligament attachment at particular time intervals during a walking gait. Thus, the force vectors as a function of time may be used to generate displacement values as a function of time. By replacing the data representing the actual joint components in the kinematic simulator with a set of implant model data and applying the force vectors, the kinematic simulator generates dynamic response data for evaluation by the dynamic response data analyzer.

These dynamic response data may be used to evaluate the motion of the joint components as a function of time during various joint movements. Such evaluations enable implant designers to obtain a likely view of how the implant components will move within the joint following replacement surgery. The simulation of the joint with the implant model enables the designers to see whether the implant supports a normal range of motion and whether adjustments need to be made in the positioning of the implant in the joint for proper joint movement. Identification of a conditional parameter may be used to generate a set of differential dimensional data to alter the set of model data so the conditional parameter may be reduced. Because the differential data may result in changes in the dynamic response data at other positions, the differential data are incorporated in the implant model data by the implant model generator to generate another set of model data for evaluation. By repeating the process, model modifications may be more fully evaluated for fit throughout a range of motion for a joint.

A method that operates in accordance with the principles of the present invention analyzes anthropometric static image data to generate a plurality of geometric dimensions and a range of dimension measurements, generates a set of implant model data from the plurality of geometric dimensions and the range of dimension measurements, simulates kinematic motion of a joint with the set of implant model data to generate dynamic response data representative of artificial implant component movement within a reconstructed joint. The method may also generate differential data in response to dynamic response data that indicates a conditional parameter occurs in at least some portion of the simulated kinematic motion of the joint. The generation of the set of model data may also include incorporating positional data from images of a joint in motion, such as fluoroscopic images of the joint in motion. These data of a joint in motion may be used to verify the dimensions of the implant model. Additionally, the inclusion of the positional data in the form of the fluoroscopic data reduces the likelihood that the set of model data modified by the differential data only conforms to the joint emulated by the kinematic simulator.

Preferably, the fluoroscopic image data are used in a patient model to generate emulation force parameters for the kinematic simulator. These emulation force parameters enable a different joint simulation in the kinematic simulator so that the simulation covers a broader range of the patient population. This use of the fluoroscopic data is preferred over the use of the positional data as verification of the artificial implant dimensions in the artificial implant model generator discussed above.

A system made in accordance with the principles of the present invention may be used for developing an artificial implant model from joint motion image data. The system includes a motion data analyzer, an anthropometric data analyzer, an artificial implant model generator, and a kinematic model simulator. The motion data analyzer receives joint motion image data, such as the fluoroscopic image data, for analysis. Motion data analyzer may perform frequency distribution analysis on the motion data to group the joint motion studies into sets that are correlated by the degree of motion demonstrated during a particular activity, such as walking or running. The correlation of images to a particular motion grouping is provided to the anthropometric data analyzer. For each motion grouping, the anthropometric data analyzer determines whether one or more geometric dimension groupings correlate to the joints depicted in the image studies associated with a motion grouping. From the geometric dimensions and their measurement range, the artificial implant model generator generates model data for an artificial implant. The model data along with the dimensions used to construct the model and the measurement ranges for the dimensions are provided to the kinematic model simulator. The dynamic response data generated from a simulation are provided to the motion data analyzer. The motion data analyzer compares the motion versus time response data received from the kinematic model simulator with the motion versus time data from at least one of the joint motion image studies correlated to the motion grouping that was used to develop the solid implant model data. The comparison determines whether the implant model was able to replicate the same range of motion as the normal knee in the correlated joint motion study. If the comparison indicates the implant model was unable to achieve the normal joint motion, a set of differential data is generated and provided to the implant model generator for development of another set of model data. The process implemented by the system may iteratively continue until a set of model data is generated that produces dynamic response data indicative of a normal range of motion. This set of model data may then be used to fabricate an artificial implant that is more likely to provide a normal range of motion in the segment of the population that corresponds to the geometric dimensions and measurements used to generate the artificial implant.

Thus, the system and method of the present invention enable the designing of an artificial implant component so that dynamic movement is incorporated within the artificial implant dimensions.

The system and method of the present invention improve the likelihood that an artificial implant component will not interfere with the smooth operation of articulating surfaces of artificial implants and will cooperate with a patient's ligament and musculature.

The above described features and advantages, as well as others, will become more readily apparent to those of ordinary skill in the art by reference to the following detailed description and accompanying drawings.

BRIEF DESCRIPTION OF THE DRAWINGS

FIGS. 6 and 6*a* are illustrations of an example of geometric dimensions that may be used for simulation of a knee compartment;

FIGS. 7 and 7*a* are illustrations of an example of geometric dimensions that may be used for simulation of a knee compartment;

FIG. 10 is a table of an example of geometric dimensions and measurement ranges for the geometric dimensions that may be used for simulation of a knee compartment;

DETAILED DESCRIPTION

Figure 1:
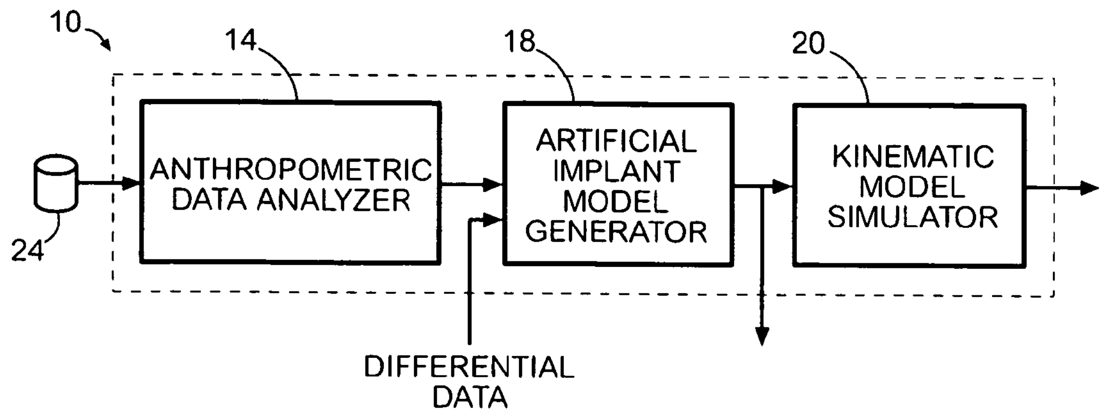
FIG. 1 is a depiction of a system made in accordance with the principles of the present invention to generate model data for the fabrication of artificial implants to be used in joint replacement surgery.

A system 10 for generating model data to fabricate an artificial implant component for a joint reconstruction is shown in FIG. 1. The system 10 includes an anthropometric data analyzer 14, an artificial implant model generator 18, and a kinematic model simulator 24. The anthropometric data analyzer 14 receives static image data, such as CT data, from a database 24. Preferably, the anthropometric data analyzer 14 performs a frequency distribution analysis on the static image data to generate one or more groupings of geometric dimensions and dimensional measurement ranges that are provided to artificial implant model generator 18. Preferably, artificial implant model generator 18 uses at least one grouping of geometric dimensions and measurement ranges to generate an implant model data set that may be used to fabricate a solid model of an artificial implant.

The kinematic model simulator 20 of the system 10 is a computer program that simulates a joint in dynamic motion. The kinematic model simulator 20 is programmed to emulate the movement of a joint in at least one particular person. That is, the data used for emulating the joint was derived from measured observations of a particular person's joint in motion. The program uses empirical measurements of forces generated at various points on a subject's body to identify emulation forcing parameters that act on the various components of a joint compartment. Such programs have been developed by various institutions, such as the University of Colorado, the University of Tennessee, and the University of Southhampton. In the system 10, the artificial implant model is used in the kinematic model simulator 20 to describe components in a joint compartment and then the emulation forcing parameters are applied to components. Data describing the movement of the components is generated from the simulation. These dynamic response data may be evaluated to determine whether the implant model data set enables a normal range of motion in a patient. This evaluation may be done by hand or by visual observation of images of the kinematic simulation. From this evaluation, differential data may be derived for incorporation by the implant model generator into the original implant model data set. This feedback enables the system 10 to generate an artificial implant model that is more likely to provide a normal range of movement for the population segment that corresponds to the frequency distribution grouping from which it was developed.

Figure 2:
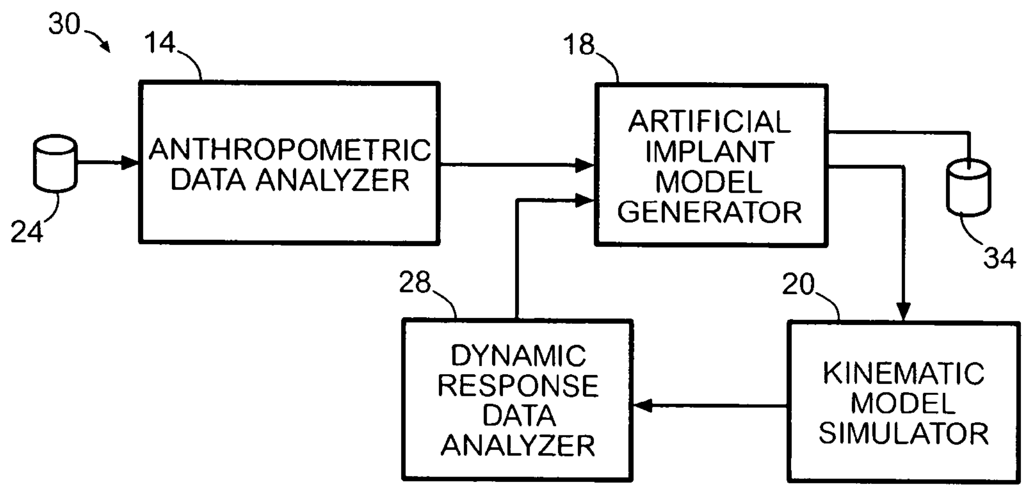
FIG. 2 is a depiction of an alternative system made in accordance with the principles of the present invention to generate model data for the fabrication of artificial implants to be used in joint replacement surgery.

An alternative system 30 is shown in FIG. 2. Using like numerals for like components, the system 30 is comprised of an anthropometric data analyzer 14, an artificial implant model generator 18, a kinematic model simulator 20, and a dynamic response data analyzer 28. The anthropometric data analyzer 14 performs analysis on the static image data received from database 24 to generate a set of dimensions and measurement ranges as discussed above. One or more groupings are used by artificial implant model generator 18 to generate a set of implant model data. The system 30 also includes a database 34 in which image data of one or more joints in motion are stored. This image data may, for example, include fluoroscopic data of a joint in motion. The implant model generator may use the image data from the database 34 to determine whether the implant components corresponding to the generated set of model data are likely to result in a conditional parameter during movement of the joint compartment. At least one set of implant model data is provided to the kinematic model simulator 20 for simulation of joint movement with the set of implant model data.

The dynamic response data generated by the kinematic model simulator 20 is provided to dynamic response data analyzer 28 to determine whether a conditional parameter between joint components appears likely. If possible undesired conditional parameters are detected, differential data are generated that would reduce an implant dimension likely to cause the detected conditional parameter. These differential data may be provided to the implant model data generator 18 to generate a second set of data that is less likely to produce the conditional parameter previously detected by the dynamic data analyzer 28. The new set of model data is used by the simulator 20 to generate dynamic response data describing the positions of the solid model with respect to time so that the dynamic response data analyzer 28 may detect whether a conditional parameter is detected.

Conditional parameters are conditions that may occur during a joint simulation that indicate one or more problems may arise from the implantation of an artificial joint fabricated from the set of model data that was used to generate the simulation. Examples of conditional parameters for which the dynamic response data may be analyzed include motion interference, economy of motion, reduction of jerk, normality of ligament tension, evenness of load sharing, minimization of energy consumption, path matching of motion, limited motion envelope, dynamic stability, reduced sensitivity to a change such as soft tissue injury or degradation, avoidance of stress peaks, controlled stress pattern, improved bone growth response, and optimal fitting. A conditional parameter for a kinematic simulation may incorporate one or more of these parameters. Simulation data indicative of a conditional parameter are studied to generate a set of differential data for modifying the set of model data to reduce the likelihood that the conditional parameter occurs.

Figure 3:
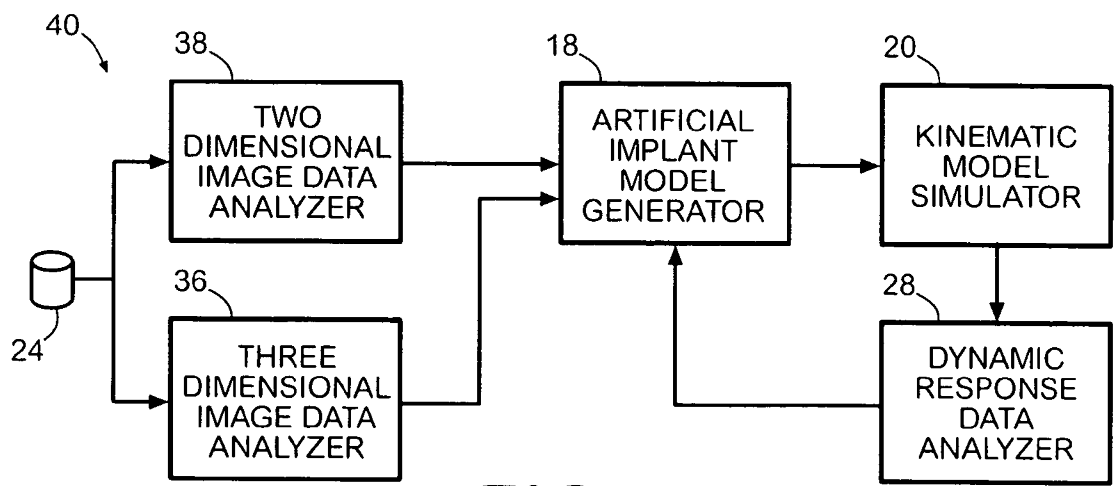
FIG. 3 is a depiction of another alternative system made in accordance with the principles of the present invention to generate model data for the fabrication of artificial implants to be used in joint replacement surgery.
Figure 4:
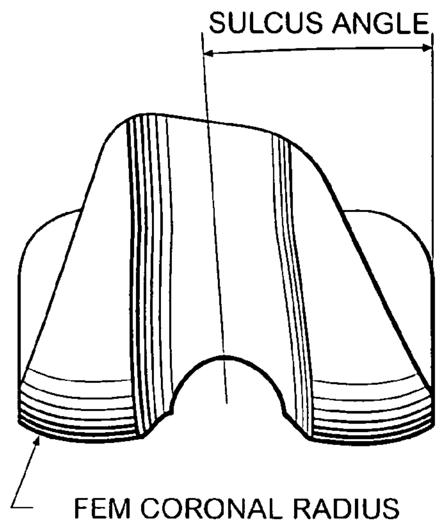
FIGS. 4 and 4*a* are illustrations of an example of geometric dimensions that may be used for simulation of a knee compartment.
Figure 4A:
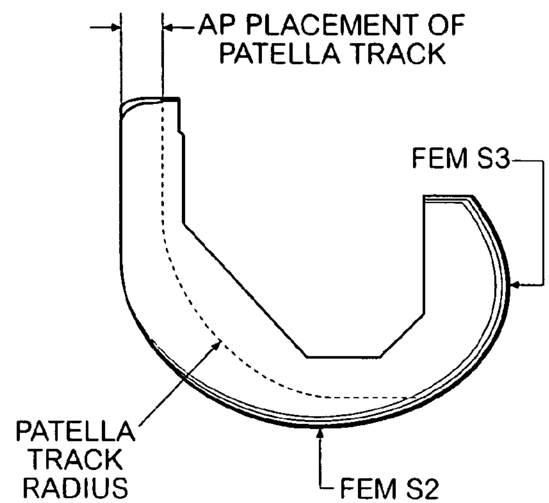

Another alternative system 40 is shown in FIG. 3. Using like numerals for like components, the system 40 includes an image database 24, an artificial implant model generator 18, a kinematic model simulator 20, and a dynamic response data analyzer 28. In system 40, the anthropometric data analyzer may be implemented with a two dimensional image data analyzer 38 and a three dimensional image data analyzer 36. The data analyzers 36 and 38, preferably, perform frequency distribution analysis on the image data from database 24. However, the two dimensional image data is provided to the two dimensional data analyzer 38 while the three dimensional image data analyzer 36 receives three dimensional image data or generates its own three dimensional data. For example, three dimensional image data analyzer 36 may generate voxel data from two dimensional image slices from a computed tomography (CT) series. The groupings of geometric dimensions and dimension measurements are provided to the implant model generator 18 for generation of an implant model. The generated model is simulated by kinematic model simulator 20 and the resulting response data are analyzed by dynamic response generator 28 to determine whether additional adjustments are required for the implant model. Although the system 40 is shown without the image database 34, it may be included in the system for generation of the implant model. Also, either the two dimensional image data analyzer 38 or the three dimensional image data analyzer 36 may be used alone for an analysis of the anthropometric data from database 24.

The anthropometric data analyzer 14, the two dimensional static data analyzer 38, the three dimensional static data analyzer 36, the model data generator 18, the kinematic model simulator 20, and the dynamic response data analyzer 28 are all preferably implemented as computer programs. These programs may all be stored and executed on a single computer in a sequential manner. Alternatively, one or more of the programs may be stored and executed on independent computer systems. The static image data analyzers 14, 36, and 38 may be implemented with a CAD program that executes on a single computer system such as the one sold by Unigraphics Solutions, Inc. of Cypress, Calif. A CAD system has an interface for receiving CT, MRI, or other similar image data from a database. An operator may then view an image of a bone on the system and select points to define a geometric dimension on the image. Once the geometric dimension is defined, the system measures and stores the dimension in a file.

A CAD system may be used to perform the frequency distribution analysis and generate the geometric dimensions and range of measurements from the anthropometric image data. For this type of use, the static image data, such as CT data, may be converted into volumetric data, sometimes called voxels, for analysis. However, curve fitting to define a geometric dimension in the three dimensional image domain may be more difficult than the defining of a geometric dimension in the two dimensional domain so a CAD system may be inadequate for some joint geometries. To address the added complexity in the three dimensional images, a computer program may be used that is specifically designed to define a surface image from a three dimensional image and measure distances between points on the surface. For example, computer programs have been developed that generate topographical surface images of terrain from satellite image data. These programs may be used to measure distances between points on the topographical surface images. One such program is the 3D topography mapping program developed by the University College of Dublin, Ireland, which may be obtained under license from the University. Another computer program that may be adapted to accept CT scan data and generate a surface model for the purposes discussed above is the Terramodel program available from Trimble Navigation Limited of Sunnyvale, Calif. Also, as known in the field, Moire analysis may be performed on the image data to empirically determine the geometric dimensions and measurement ranges.

The model data generator 18 may be implemented by a surface modeling program such as the Unigraphics CAD system or Terramodel system noted above. Model data generator 18 receives a data grouping defining a plurality of geometric dimensions and the range of measurements for each dimension to generate a solid model of one or more artificial implant components for a joint. Additionally, model data generator 18 may also receive two dimensional data of one or more joints in dynamic motion. For example, database 34 may store image data of a joint in motion as depicted in a series of fluoroscopic images taken at a defined rate, such as 20 images/second. The two dimensional image data of the joint in motion provide positional information of surface points as the joint is moved. These data may be used by the model data generator 20 to determine whether a set of model data developed from the geometric dimensions and range data indicates a conditional parameter may arise from the implantation of an artificial joint corresponding to the set of model data. If so, the model data may be modified to reduce the likelihood of the detected conditional parameter. Preferably, the two dimensional image data of the joint in motion includes image data for a plurality of subjects so that a range of joint geometries representative of a broader spectrum of the population is used for adjusting the solid model data. In this manner, solid models are generated that are more likely to fit a larger number of people rather than only those persons having an anatomical structure that is similar to the joint images for a single subject.

The kinematic model simulator 20 may be a computer program that simulates the movement of a joint within a particular person. The simulator 20 applies emulation force parameters to the simulated knee geometry and generates response data corresponding to the movement of the joint components. These response data generated by the simulator 20 are in the time domain and may be evaluated to determine whether the components in the implant joint compartment interfere with one another. The results of the evaluation may be used to determine the alterations required for a better fitting and/or performing artificial joint implant.

Figure 5A:
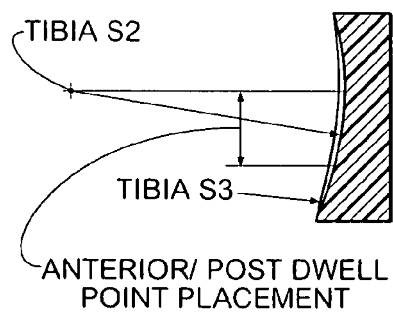
FIGS. 5, 5*a*, and 5*b* are illustrations of an example of geometric dimensions that may be used for simulation of a knee compartment.
Figure 5:
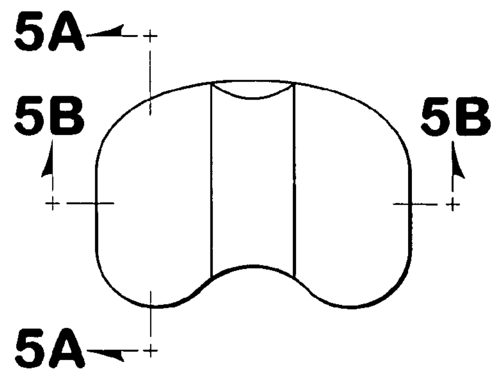
Figure 5B:
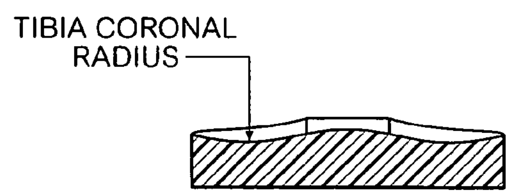
Figure 8:
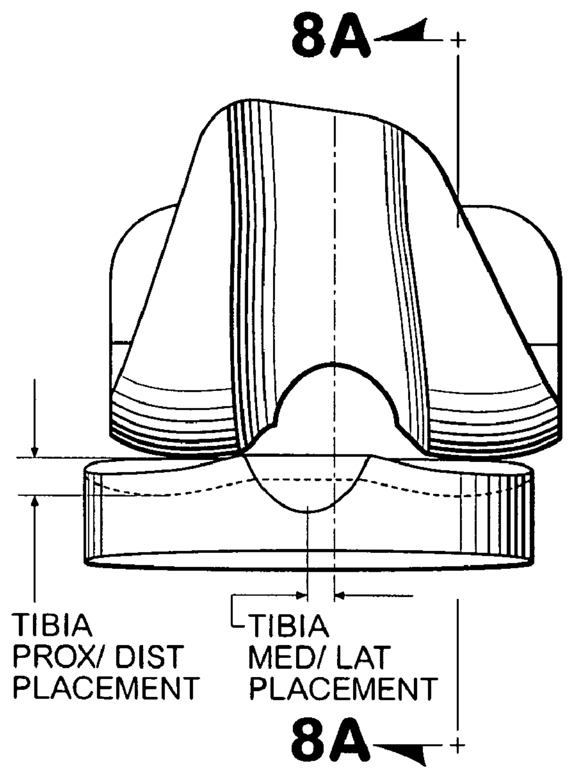
FIGS. 8 and 8*a* are illustrations of an example of geometric dimensions that may be used for simulation of a knee compartment.
Figure 8A:
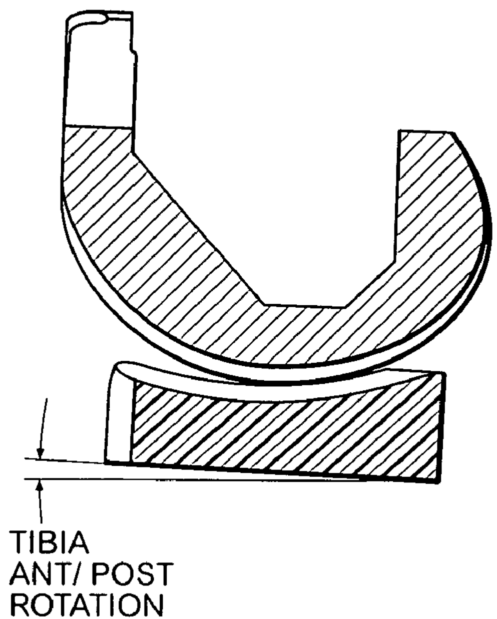
Figure 9:
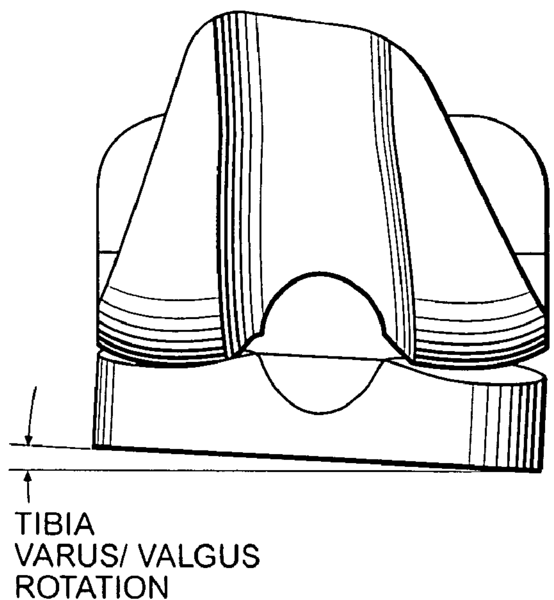
FIGS. 9 and 9*a* are illustrations of an example of geometric dimensions that may be used for simulation of a knee compartment.
Figure 9A:
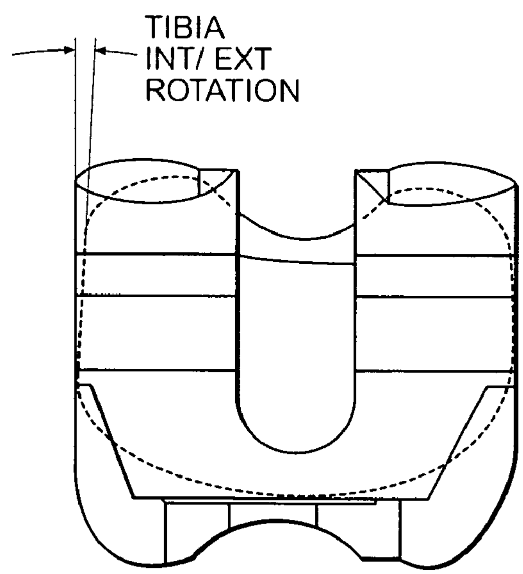

FIGS. 4-9 and their accompanying cross-sectional drawings contain examples of geometric dimensions for a knee compartment. In FIG. 5, the sagital conformity is approximately equal to the tibia S2/femoral S2 ratio and the coronal conformity is approximately equal to the tibia coronal radius/femoral coronal radius ratio. Although the dimensions depicted in these drawings are preferred geometric dimensions for knee compartment analysis, other geometric dimensions may be used. Also, these dimensions are examples of the types of geometric dimensions that may be used to simulate other joint compartments. Preferably, these geometric dimensions are also provided to the simulator 20 with the measurement range for the dimensions so the dimensions may be altered for multiple simulations. A list of examples of geometric dimensions and their corresponding ranges are shown in FIG. 10.

The geometric dimensions may be monitored during a joint simulation to evaluate the articulation between components in a simulated knee compartment. To facilitate the accumulation of simulation data, these geometric dimensions may be selectively altered to different values within a measurement range for the dimension. These different implant models are simulated with the simulator 20 to generate response data for the various implant models. Preferably, the different values for a different geometric dimension are selected to provide points for interpolation for model simulations that were not specifically emulated. Thus, the simulator 20 may be used to determine response data for implant models other than the ones specifically emulated. The selection of geometric dimensions for alteration to generate multiple simulations is known as a design of experiment (DOE) approach. The dynamic response data for each simulation are stored for evaluation by the dynamic data analyzer so an optimal implant model may be selected.

Figure 11:
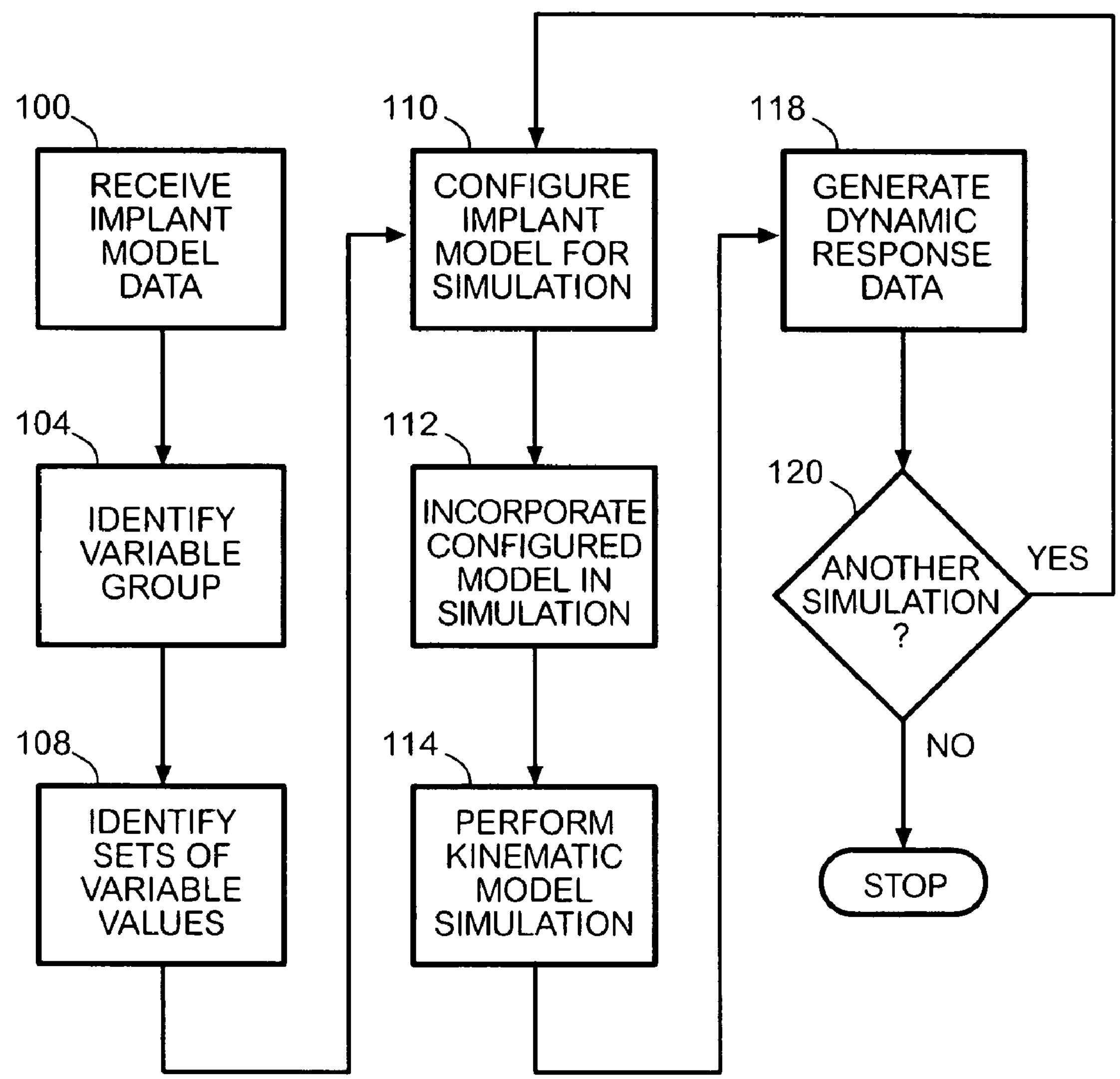
FIG. 11 is a flow diagram of an example of processing performed by the kinematic model simulator of the system shown in FIGS. 1, 2, 3, and 13.

An example of a method performed by the kinematic model simulator 20 is shown in FIG. 11. In the method, the simulator 20 receives the solid model data (block 100). A group of variables for the geometry of the solid model data is identified (block 104) and discrete sets of values within a measurement range for each dimension are defined for multiple simulations of the joint (block 108). A set of values is used to configure the solid data model for a simulation (block 110) and the configured solid data model substituted into the simulator for the data defining the joint around which the simulator was developed (block 112). The simulation is performed (block 114) and the generated dynamic response data describing the simulation are stored (block 118). The process determines whether another simulation is to be performed (block 120). If it is, then another set of values are used to re-configure the solid model data (block 110) and another simulation performed to generate dynamic data for the simulation (blocks 112-118). A simulation is performed for each set of values until all of the sets have been used.

The dynamic response data analyzer 28 is a computer program that evaluates the dynamic response data generated by the simulator 20. One type of evaluation performed by the dynamic data analyzer 28 is the detection of a conditional parameter from the dynamic response data. That is, analyzer 28 determines whether positional or other data in the dynamic response data for a simulation indicates a conditional parameter is likely to arise from the implantation of the artificial joint corresponding to the set of model data used to generate the simulation. The analyzer 28 also interpolates between the sets of dynamic data to determine whether a more optimal configuration for the model data may exist at a point that corresponds to a set of values not specifically simulated. In response to detection of a conditional parameter or identification of another set of values generating a more optimal dynamic data response, the dynamic data analyzer 28 generates a set of differential data that may be applied to the solid model data to modify the measurements of the geometric dimensions. These differential data may be provided to the model data generator 18 so that a second set of model data may be generated and the kinematic model simulation repeated for evaluation of the new solid model. This process may be continued until the differential data is less than an acceptance parameter, such as a measurable threshold. Alternatively, the process may be stopped in response to no detection of a conditional parameter or no identification of a more optimal set of variable values for the solid model data.

Figure 12:
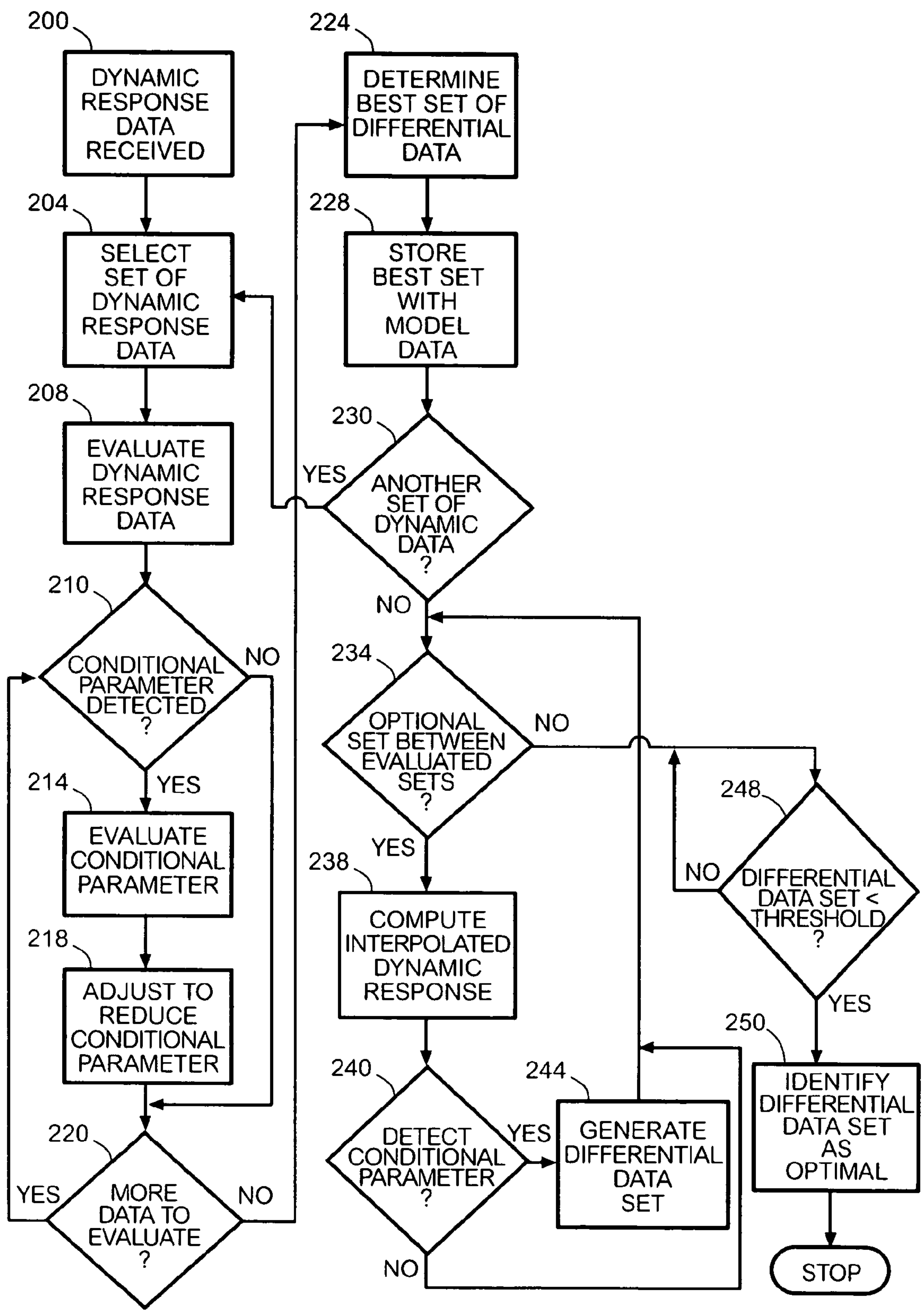
FIG. 12 is a flow diagram of an example of processing performed by the dynamic data analyzer of the system shown in FIGS. 1, 2, 3, and 13.

An example of a process performed by the dynamic response data analyzer 28 is shown in FIG. 12. In the process, sets of dynamic data are received from the kinematic model simulator 20 (block 200). A set of dynamic data is selected for evaluation (block 204). Response data for each time interval in the set of dynamic data is evaluated to determine whether a conditional parameter occurred (block 208). If a conditional parameter is detected (block 210), the surrounding dynamic data are evaluated (block 214). To this overlap area, a clearance margin is added to generate a set of differential data (block 218). The process determines whether additional dynamic data in the data set requires evaluation (block 220). If it does, the process continues looking for conditional parameters (block 210) and computing differential data sets (blocks 214-218) until all of the dynamic data in a set of dynamic data for a simulation has been evaluated (block 220). When no further data in a set is available for processing, the process compares the sets of differential data and determines which one or which combination of differential data sets is required to adjust the solid model so no conditional parameter would have occurred (block 224). This set of differential data is stored in association with the solid model data that was used to perform the simulation (block 228). If additional data sets are available, another set of data is selected (block 204) and the process continues to generate a set of differential data if a conditional parameter is detected (blocks 208-224). After all sets of dynamic data are processed, trending or minimum techniques may be used to determine whether a minimum for a set of differential data may exist for a set of solid model variables between two known sets (block 234). If a determination is made that a minimum set may exist, an interpolated dynamic data set is computed (block 238) and the dynamic data of this set is evaluated for conditional parameters (block 240). The process of searching for a minimum differential data set continues until no further candidates are identified (blocks 234). Each differential data set may be compared to a differential threshold (block 248). If the differential data are less than the differential threshold, the set of corresponding solid model variable values is identified as an optimal set (block 250). This set may then be used by the solid model data generator for another solid model data set that may be simulated and further evaluated.

Figure 13:
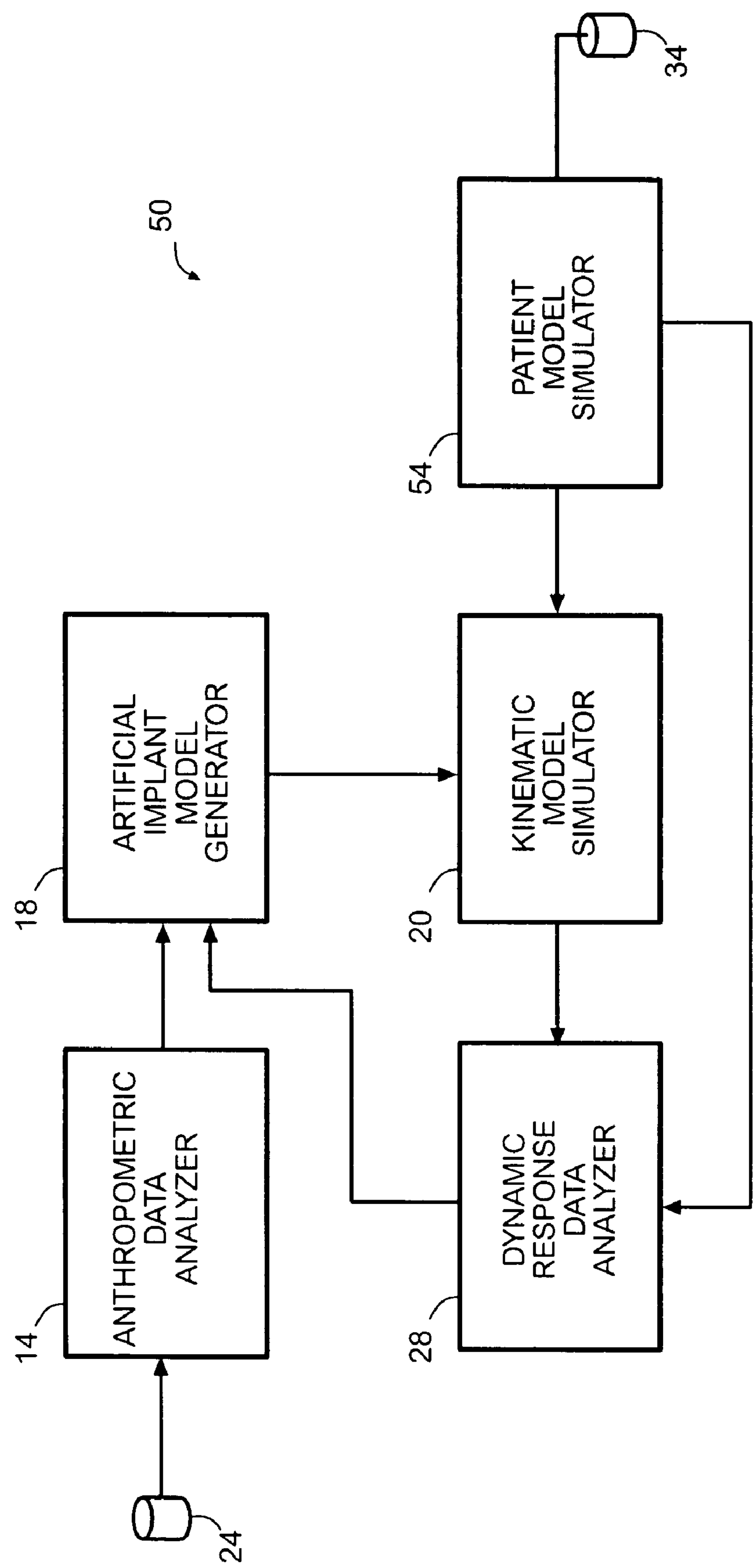
FIG. 13 is a depiction of another system made in accordance with the principles of the present invention to generate model data for the fabrication of artificial implants to be used in joint replacement surgery.

A more preferred embodiment of the present invention is shown in FIG. 13. Using like numerals for like components, the system 50 includes an anthropometric data analyzer 14, an artificial implant model generator 18, a kinematic model simulator 20, a dynamic response data analyzer 28, and a patient model simulator 54. The anthropometric data analyzer 14 may be implemented with a two dimensional data analyzer 38, a three dimensional data analyzer 36, or both. The patient model simulator 54 receives static image data of a joint in motion, such as fluoroscopic image data, from a database 34. The patient model simulator 54 is a computer program that takes data in the time domain that may be obtained from the joint motion image data and analytically solves for the forces being exerted at various points of the joint component geometry. The forces may then be provided to the kinematic model simulator 20 as emulation force parameters. The emulation force parameters are substituted for the force functions used by the kinematic model simulator 20 for generating simulations. That is, the patient model simulator 54 converts the motion versus time data of the joint motion image data into force versus time data that may be used by the kinematic model simulator 20 for performing simulations. This method provides at least two advantages. For one, the simulations performed by the kinematic model simulator 20 may now be varied to correspond to different knee image studies. For another, the motion versus time data (dynamic response data) generated by the kinematic model simulator 20 may now be compared to the motion versus time data used by the patient model simulator 54 to generate the emulation force parameters. By comparing the two sets of motion versus time data, the dynamic data analyzer may determine whether the simulated motion of the implant model moved in a manner that correlates to the movement of the joint in a healthy patient. In systems 10, 30, and 40, there was no standard against which the motion versus time data generated by the kinematic simulator 20 could be compared. With the system 50, the same forces that caused the movement captured in the joint motion image data of database 34 may be used in the simulator 20 to increase the range of its simulation and provide a benchmark for dynamic response data comparisons. The differences between the response data generated by the kinematic model simulator 20 and the response data used by the patient model simulator 54 may be used to generate differential data for modifying the implant model. The adjustments made to the implant model based on the comparison with the joint motion image data help ensure a solid joint implant model that is more likely to enable a normal range of motion following surgery.

Figure 14:
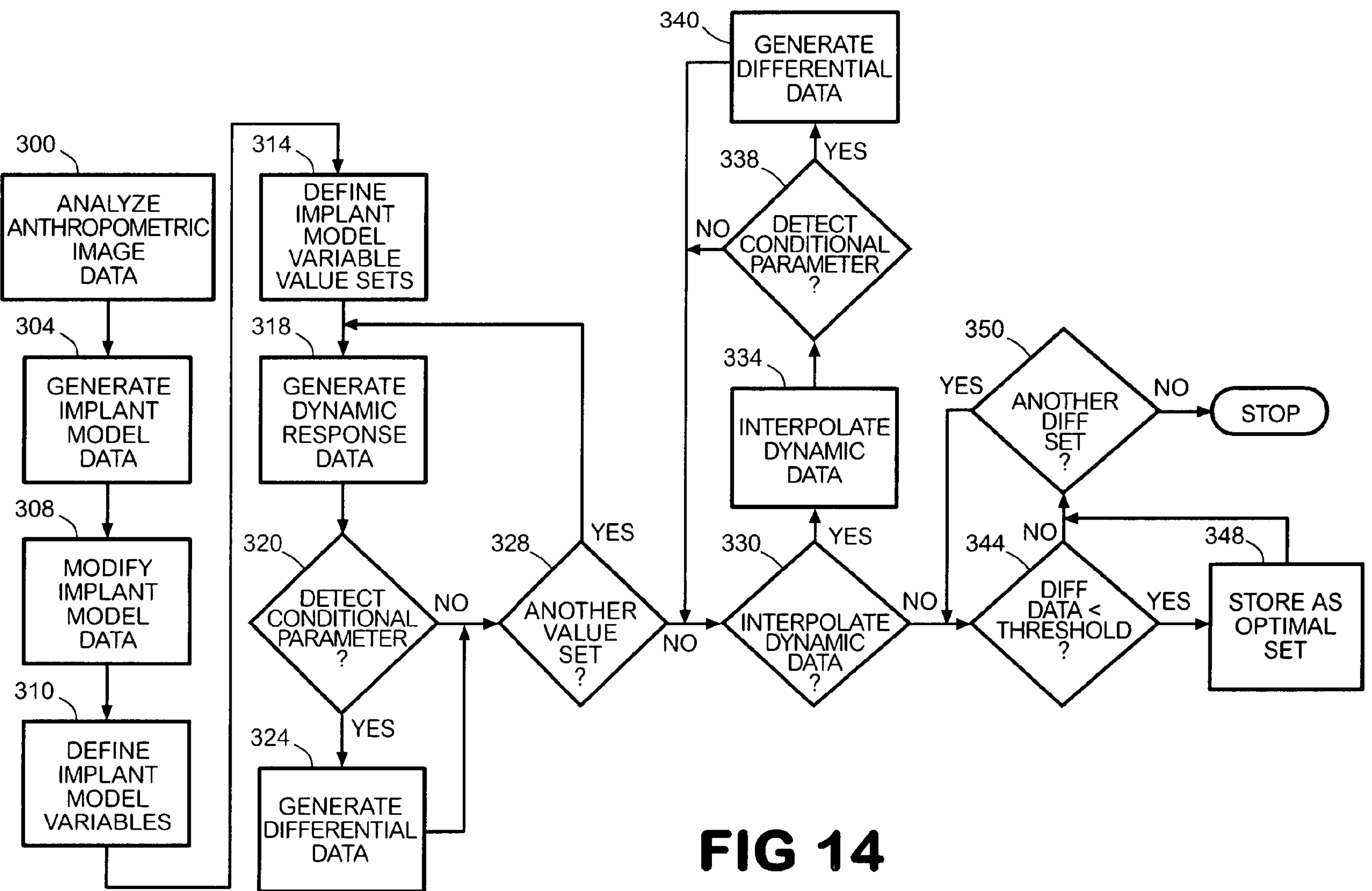
FIG. 14 is a flow diagram of the overall methodology implemented by the systems shown in FIGS. 1, 2, 3, and 13.

An example of a process that may be performed by the system 10 is shown in FIG. 14. Anthropometric image data of joints are analyzed to generate a set of geometric dimensions and a range for each dimension (block 300). These dimensions and measurement ranges are used to generate solid model data (block 304). The solid model data may be modified with reference to image data of one or more joints being operated through a range of motion (block 308). The modified solid model data dimensions are measurement ranges are provided to the implant model generator to define a set of model variables (block 310). Multiple sets of variable values for the variables for a joint simulation are defined (block 314). Each set of values is used to generate a corresponding set of dynamic response data (block 318). Each set of dynamic response data is evaluated for detection of a conditional parameter and/or compared to positional data used to generate emulation force parameters (block 320). From the evaluation or comparison, a set of differential data is generated for modification of the solid model data to attenuate the probability of the conditional parameter occurring (block 324). This part of the process continues as long as another set of variable values is available for generation of dynamic response data (block 328). The sets of differential data are evaluated to determine whether interpolated variable value sets may generate more optimal solid model data (block 330). If interpolation is indicated, the dynamic response data is interpolated (block 334) and evaluated for detection of a conditional parameter (block 338). Differential data sets are generated in response to the detection of conditional parameters (block 340). Each differential data set is compared to threshold criteria to determine whether an optimal solid model data set has been obtained (block 344). If it is optimal, the data set is stored (block 348). The process continues until all of the differential data sets are compared to the threshold (block 350).

Figure 15:
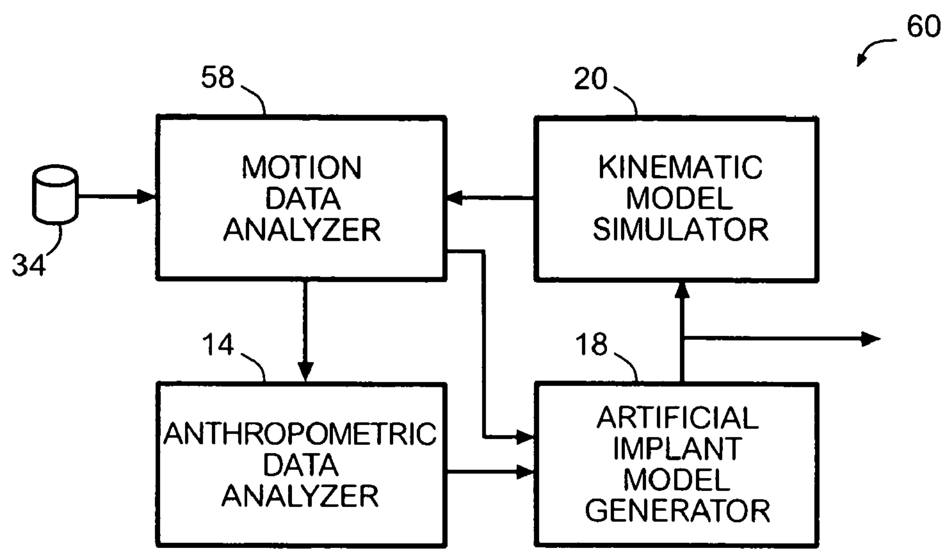
FIG. 15 is a depiction of another system made in accordance with the principles of the present invention to generate model data for the fabrication of artificial implants to be used in joint replacement surgery.

A system for developing solid model data from joint motion image data is shown in FIG. 15. Using like numerals for like components, the system 60 includes a motion data analyzer 58, an anthropometric data analyzer 14, an artificial implant model generator 18, and a kinematic model simulator 20. The motion data analyzer 58 receives joint motion image data, such as the fluoroscopic image data previously described, for analysis. Motion data analyzer 58 preferably performs frequency distribution analysis on the motion data to group the joint motion studies into sets that are correlated by the degree of motion demonstrated during a particular activity, such as walking or running. The correlation of images to a particular motion grouping is provided to the anthropometric data analyzer 14. For each motion grouping, the anthropometric data analyzer determines whether one or more geometric dimension groupings correlate to the joints depicted in the image studies associated with a motion grouping. From the geometric dimensions and their measurement range, the artificial implant model generator 18 generates model data for an artificial implant. The model data along with the dimensions used to construct the model and the measurement ranges for the dimensions are provided to the kinematic model simulator 20. The dynamic response data generated from a simulation are provided to the motion data analyzer 58. The motion data analyzer compares the motion versus time response data received from the kinematic model simulator with the motion versus time data from at least one of the joint motion image studies correlated to the motion grouping that was used to develop the solid implant model data. The comparison determines whether the implant model was able to replicate the same range of motion as the normal knee in the correlated joint motion study. If the comparison indicates the implant model was unable to achieve the normal joint motion, a set of differential data is generated and provided to the implant model generator 18 for development of another set of model data. The process implemented by the system 60 may iteratively continue until a set of model data is generated that produces dynamic response data indicative of a normal range of motion. This set of model data may then be used to fabricate an artificial implant that is more likely to provide a normal range of motion in the segment of the population that corresponds to the geometric dimensions and measurements used to generate the artificial implant.

Figure 16:
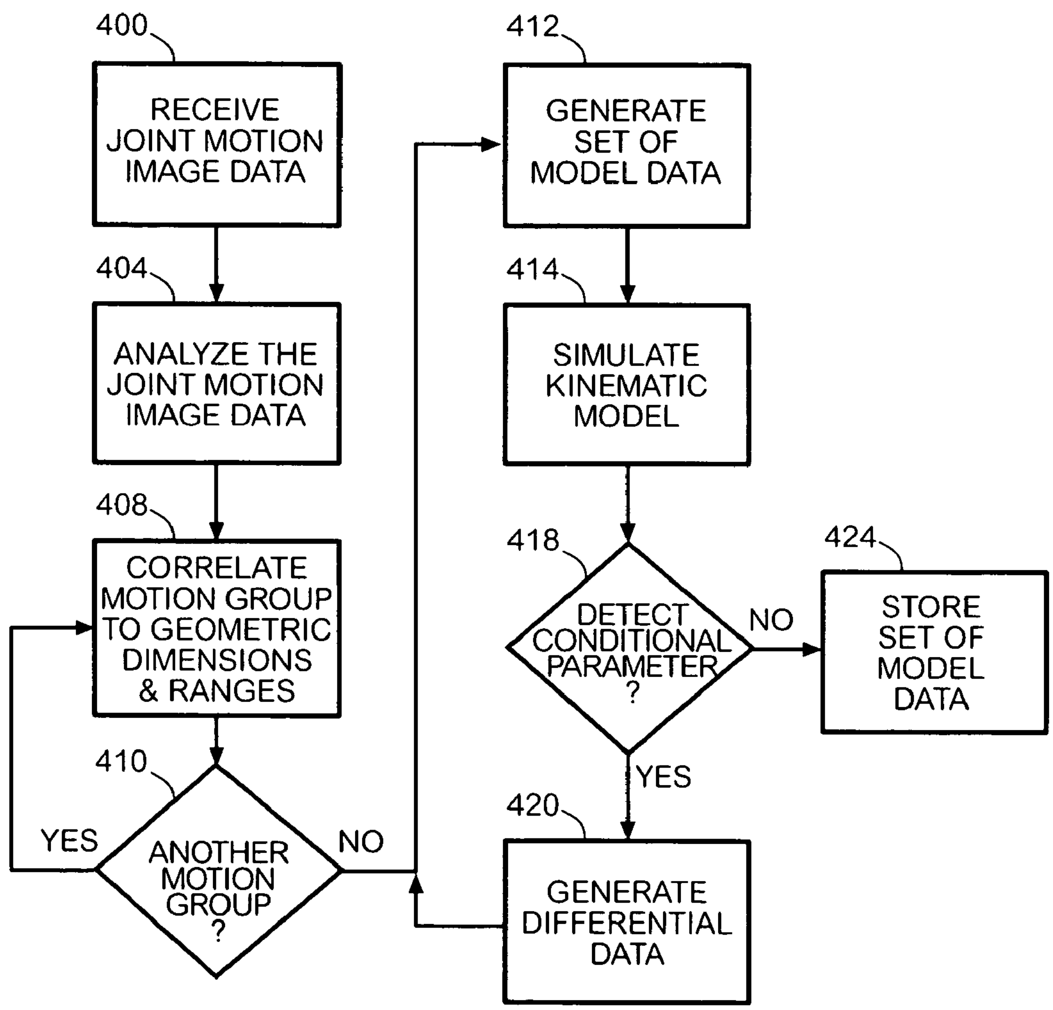
FIG. 16 is a flow diagram of an example of a process implemented by the system shown in FIG. 15.

A method for developing solid model data from joint motion image data is shown in FIG. 16. The method includes receiving joint motion image data (block 400), such as the fluoroscopic image data previously described, for analysis. The motion data is analyzed to group the joint motion studies into sets that are correlated by the degree of motion demonstrated during a particular activity, such as walking or running (block 404). This analysis may be performed by frequency distribution analysis, for example. The correlation of images to a particular motion grouping is then analyzed by determining whether one or more geometric dimension groupings correlate to the joints depicted in the image studies associated with a motion grouping (block 408). This analysis is performed for each motion grouping (block 410). From the geometric dimensions and the corresponding measurement range for each dimension, the artificial implant model generator 18 generates model data for an artificial implant that corresponds to a motion grouping (block 412). The model data along with the dimensions used to construct the model and the measurement ranges for the dimensions are used for a kinematic model simulation (block 414). The dynamic response data generated from a simulation are compared to one or more joint motion image studies to determine whether a conditional parameter is detected (block 418). This comparison may be between the motion versus time response data from the kinematic model simulation and the motion versus time data from at least one of the joint motion image studies correlated to the motion grouping that was used to develop the solid implant model data. The comparison determines whether the implant model was able to replicate the same motion as the normal knee in the correlated joint motion study. If the comparison indicates the implant model was unable to achieve the normal joint motion, a set of differential data is generated (block 420) and used to develop another set of model data. The process may iteratively continue until a set of model data is generated that produces dynamic response data indicative of a normal range of motion. This set of model data may then be stored (block 424) and later used to fabricate an artificial implant that is more likely to provide a normal range of motion in the segment of the population that corresponds to the geometric dimensions and measurements used to generate the artificial implant.

While the present invention has been illustrated by the description of examples of processes and system components, and while the various processes and components have been described in considerable detail, applicant does not intend to restrict or in any limit the scope of the appended claims to such detail. Additional advantages and modifications will also readily appear to those skilled in the art. Therefore, the invention in its broadest aspects is not limited to the specific details, implementations, or illustrative examples shown and described. Accordingly, departures may be made from such details without departing from the spirit or scope of applicant's general inventive concept.

What is claimed is:

1. A computer system that generates a set of artificial implant model data used to fabricate an artificial implant that provides a set of ranges of motions for a joint depicted in joint motion image data for a plurality of corresponding joints in a plurality of subjects comprising:

an anthropometric data analyzer executing on a computer for receiving joint motion image data representative of the plurality of corresponding joints in the plurality of subjects, and the received data being displayed by the anthropometric analyzer on a display to enable an operator to select points that identify a plurality of geometric dimensions and ranges of values for the identified geometric dimensions;

an implant model generator executing on the computer, the implant model generator receiving the identified geometric dimensions and the ranges of values for the identified geometric dimensions that were generated by the anthropometric data analyzer and generating a set of artificial implant model data for fabricating the artificial implant that corresponds to the identified geometric dimensions and a set of discrete values for the identified geometric dimensions for the artificial implant from the identified geometric dimensions and the ranges of values for the identified geometric dimensions;

a kinematic model simulator executing on the computer, the kinematic model simulator incorporating the set of artificial implant model data generated by the implant model generator in a kinematic model of the joint, and simulating movement of the joint with the kinematic model to generate motion versus time data;

a motion data analyzer executing on the computer that compares the motion versus time data generated by the kinematic model simulator with motion versus time data from the joint motion image data used to identify the geometric dimensions and the ranges of values for the identified geometric dimensions that were used to generate the set of artificial implant model data to determine whether the artificial implant corresponding to the set of artificial implant model data provides the set of ranges of motions for the joint depicted in the joint motion image data; and a database coupled to the computer executing the motion data analyzer to receive and store the set of artificial implant model data in a database file, in response to the motion data analyzer determining the artificial implant corresponding to the set of artificial implant model data provides the set of ranges of motions for the joint depicted in the joint motion image data to enable the artificial implant model data to be retrieved for fabricating the artificial implant.

2. The computer system of claim 1 further comprising:

the motion data analyzer receives the motion versus time data generated by the kinematic model simulator and generates differential dimensional data for modifying the set of artificial implant model data in response to the motion versus time data generated by the kinematic model simulator indicating that the artificial implant corresponding to the set of artificial implant model data does not provide the set of ranges of motions for the joint depicted in the joint motion image data.

3. The computer system of claim 2 wherein the implant model generator receives the differential dimensional data from the motion data analyzer and modifies the set of artificial implant model data with the differential dimensional data to generate a second set of artificial implant model data;

the kinematic model simulator incorporates the second set of artificial implant model data in the kinematic model of the joint to generate a second kinematic model of the joint and simulates movement of the joint with the second kinematic model to generate a second set of motion versus time data;

the motion data analyzer determines whether the artificial implant corresponding to the second set of artificial implant model data provides the set of ranges of motions for the joint depicted in the joint motion image data; and the database stores the second set of artificial implant model data in a database file in response to the determination that the artificial implant corresponding to the second set of artificial implant model data provides the set of ranges of motions for the joint depicted in the joint motion image data to enable the second set of artificial implant model data to be retrieved for fabricating the artificial implant.

4. The computer system of claim 1 wherein the anthropometric data analyzer receives computed tomography (CT) data for the plurality of corresponding joints for the plurality of subjects for analysis.

5. The computer system of claim 1 wherein the anthropometric data analyzer receives magnetic resonance image (MRI) data for the plurality of corresponding joints for the plurality of subjects for analysis.

6. The system of claim 1 wherein the anthropometric data analyzer executing on the computer analyzes static image data.

7. The computer system of claim 6 wherein the anthropometric data analyzer executes on a computer aided design (CAD) system to enable the operator to select a feature in the static image data to define a geometric dimension and to measure the defined geometric dimension.

8. The computer system of claim 1 the system further comprising:

a patient model emulator executing on the computer to generate emulation force vectors that are used by the kinematic model simulator to simulate movement of the joint with the kinematic model.

9. The computer system of claim 8 wherein the patient model emulator generates the emulation force vectors from image data of the joint in motion.

10. The computer system of claim 9 wherein the patient model emulator generates the emulation force vectors from fluoroscopic image data of the joint in motion.

11. The computer system of claim 10 wherein the kinematic model simulator receives the emulation force vectors generated by the patient model emulator and applies the emulation force vectors to the kinematic model to generate motion versus time data for the simulated movement of the joint.

12. The computer system of claim 11 wherein the motion data analyzer compares the motion versus time data that was generated by the kinematic model simulator to motion versus time data from the fluoroscopic image data used to generate the emulation force vectors.

13. The computer system of claim 12 wherein the motion data analyzer generates a set of differential dimensional data for modification of the set of artificial implant model data to reduce a likelihood of motion interference occurring from an implantation of the artificial implant corresponding to the set of artificial implant model data.

14. A method for operating a computer system to generate a set of artificial implant model data used to fabricate an artificial implant that provides a set of ranges of motions for a joint depicted in joint motion image data for a plurality of corresponding joints in a plurality of subjects comprising:

displaying joint motion image data for the plurality of corresponding joints in the plurality of subjects to enable an operator to identify a plurality of geometric dimensions and ranges of values for the identified geometric dimensions;

generating the set of artificial implant model data for fabricating the artificial implant that corresponds to the identified geometric dimensions and a set of discrete values for the identified geometric dimensions for the artificial implant from the identified geometric dimensions and the ranges of values for the identified geometric dimensions;

incorporating the set of artificial implant model data in a kinematic model of the joint;

generating emulation force vectors from image data of the joint in motion;

applying the emulation force vectors to the kinematic model to simulate movement of the joint with the kinematic model and generating motion versus time data for the simulated movement of the joint;

comparing the motion versus time data generated for the simulated movement of the joint to motion versus time data from the joint motion image data used to identify the geometric dimensions and the ranges of values for the identified geometric dimensions that were used to generate the set of artificial implant model data to determine whether the artificial implant corresponding to the set of artificial implant model data provides the set of ranges of motions for the joint depicted in the joint motion image data; and storing the set of artificial implant model data in a database file in response to the determination that the artificial implant corresponding to the set of artificial implant model data provides the set of ranges of motions for the joint depicted in the joint motion image data to enable the artificial implant model data to be retrieved for fabricating the artificial implant.

15. The method of claim 14 further comprising:

generating differential dimensional data to modify the set of the artificial implant model data in response to the comparison of the motion versus time data generated from the simulated movement of the joint with the kinematic model indicating that the artificial implant corresponding to the set of artificial implant model data produces motion interference during the simulated movement of the joint with the kinematic model; and modifying the set of artificial implant model data with the generated differential dimensional data to generate a second set of artificial implant model data.

16. The method of claim 15 further comprising:

incorporating the second set of artificial implant model data in the kinematic model of the joint to generate a second kinematic model of the joint;

applying the emulation force vectors to the second kinematic model to simulate movement of the joint and generating motion versus time data for the simulated movement of the joint with the second kinematic model;

comparing the motion versus time data generated for the simulated movement of the joint with the second kinematic model to motion versus time data from the joint motion image data used to identify the geometric dimensions and the ranges of values for the identified geometric dimensions to determine whether the artificial implant corresponding to the second set of artificial implant model data provides the set of ranges of motions for the joint depicted in the joint motion image data; and storing the second set of artificial implant model data in a database file in response to the determination that the artificial implant corresponding to the second set of artificial implant model data provides the set of ranges of motions for the joint depicted in the joint motion image data to enable the second set of artificial implant model data to be retrieved for fabricating the artificial implant.

17. The method of claim 15 wherein the artificial implant model data modification includes modification of the set of artificial implant model data using fluoroscopic image data of the plurality of corresponding joints in motion from the plurality of subjects.

18. The method of claim 14 wherein the display of joint motion data includes display of computed tomography (CT) data for the plurality of corresponding joints in the plurality of subjects.

19. The method of claim 14 wherein the display of joint motion data includes display of magnetic resonance image (MRI) data for the plurality of corresponding joints in the plurality of subjects.

20. The method of claim 14 wherein the display of joint motion data includes display of three dimensional image data for the plurality of corresponding joints in the plurality of subjects.

21. The method of claim 14 wherein the display of the joint motion image data includes enabling an operator to select a feature in static image data to define a geometric dimension and to measure the defined geometric dimension.

22. The method of claim 14 wherein the comparison of the motion versus time data generated for the simulated movement of the joint to the motion versus time data from the joint motion image data includes identifying motion interference during the movement of the joint.

23. The method of claim 22 wherein the comparison of the motion versus time data generated for the simulated movement of the joint to the motion versus time data from the joint motion image data includes generating a set of differential dimensional data for modification of the set of artificial implant model data to reduce a likelihood of motion interference occurring from an implantation of the artificial implant corresponding to the set of artificial implant model data.

24. A computer system that generates a set of artificial implant model data used to fabricate an artificial implant that provides a set of ranges of motions for a joint depicted in joint motion image data for a plurality of corresponding joints in a plurality of subjects, comprising:

a motion data analyzer executing on a computer for receiving joint motion image data for the plurality of corresponding joints in the plurality of subjects, the motion data analyzer grouping the joint motion image data into sets that are correlated by ranges of motions for a particular activity for the joint depicted in the joint motion image data;

an anthropometric data analyzer executing on the computer to display one of the sets of joint motion image data correlated by the ranges of motions for the particular activity to enable an operator to identify geometric dimensions and measurement ranges of values for the identified geometric dimensions from the one set of joint motion image data;

an artificial implant model generator executing on the computer to generate a set of artificial implant model data for fabricating the artificial implant that corresponds to the identified geometric dimensions and a set of discrete values for the identified geometric dimensions for the artificial implant from the identified geometric dimensions and the measurement ranges of values for the identified geometric dimensions for the one set of joint motion image data correlated by the ranges of motions for the particular activity;

a kinematic model simulator executing on the computer, the kinematic model simulator simulating movement of the joint with the artificial implant model data received from the artificial implant model generator and generating motion versus time data from the simulated movement of the joint for the one set of joint motion image data correlated by the ranges of motions for the particular activity;

the motion data analyzer comparing the motion versus time data generated by the kinematic model simulator with motion versus time data from the one set of joint motion image data used to identify the geometric dimensions and the measurement ranges of values for the identified geometric dimensions that were used to generate the set of artificial implant model data to determine whether the artificial implant corresponding to the set of artificial implant model data provides the set of ranges of motions for the joint for the particular activity for the joint depicted in the one set of joint motion image data; and a database coupled to the computer executing the motion data analyzer, the database receiving and storing the artificial implant model data in a database file in response to the comparison of the motion versus time data indicating the artificial implant model data provides the set of ranges of motions for the joint for the particular activity for the joint depicted in the one set of joint motion image data, for later retrieval and use in fabrication of an artificial implant.

25. The computer system of claim 24 wherein the motion data analyzer receives fluoroscopic image data of the plurality of corresponding joints in motion from a database in which fluoroscopic image data are stored.

26. The computer system of claim 25 further comprising:

the motion data analyzer receives the motion versus time data from the kinematic model simulator and generates differential dimensional data for modifying the artificial implant model data in response to the comparison of the motion versus time data from the simulated movement of the joint to the motion versus time data from the one set of joint motion image data indicating that the artificial implant corresponding to the artificial implant model data does not provide the ranges of motions for the particular activity for the joint depicted in the one set of joint motion image data.

27. A method for operating a computer system to generate an artificial implant design corresponding to a set of artificial implant model data that is used to fabricate an artificial implant that provides a set of ranges of motions for a joint depicted in joint motion image data for a plurality of corresponding joints in a plurality of subjects, comprising:

executing a program on a computer to analyze joint motion image data for the plurality of corresponding joints in the plurality of subjects to group the joint motion image data into sets, each set corresponding to a set of ranges of motions for an activity for the joint depicted in the joint motion image data;

executing a program on the computer to display one of the sets of the joint motion image data to enable an operator to identify geometric dimensions and measurement ranges of values for the identified geometric dimensions, the identified geometric dimensions and measurement ranges of values for the identified geometric dimensions corresponding to the one set of joint motion image data;

executing a program on the computer to generate a set of artificial implant model data for fabricating the artificial implant that corresponds to the identified geometric dimensions and a set of discrete values for the identified geometric dimensions for the artificial implant from the identified geometric dimensions and the measurement ranges of values for the identified geometric dimensions for the one set of joint motion image data;

executing a program on the computer to incorporate the set of artificial implant model data into a kinematic model of the joint;

executing a program on the computer to simulate movement of the joint with the kinematic model of the joint and generating motion versus time data from the simulation of movement of the joint with the kinematic model of the joint;

executing a program on the computer to compare the generated motion versus time data from the simulation of movement of the joint to motion versus time data for the ranges of motions for the activity depicted in the one set of joint motion image data used to generate the set of artificial implant model data; and executing a program on the computer to store the set of artificial implant model data in a database file in response to the motion versus time data generated for the simulated movement of the joint corresponding to the ranges of motions for the activity depicted in the one set of joint motion image data, for later retrieval and use in fabrication of an artificial implant.

28. The method of claim 27 wherein the analysis of the joint motion image data performed by the computer includes receiving fluoroscopic image data of the plurality of corresponding joints in motion in the plurality of subjects.

29. The method of claim 27 wherein the comparison of the generated motion versus time data from the simulation of movement of the joint to motion versus time data for the ranges of motions for the activity depicted in the one set of joint motion image data used to generate the set of artificial implant model data includes:

generating a set of differential dimensional data in response to the comparison indicating that the artificial implant model did not correspond to the ranges of motions for the activity depicted in the one set of joint motion image data.

* * * * *